United States Patent [19]

Uchiyama

[11] Patent Number: 5,073,697
[45] Date of Patent: Dec. 17, 1991

[54] MULTI-USE TYPE HEATING APPARATUS

[76] Inventor: Gorō Uchiyama, 832-10, Oaza-Suna, Kawagoe-Shi, Saitama-Ken, Japan

[21] Appl. No.: 514,306

[22] Filed: Apr. 25, 1990

[30] Foreign Application Priority Data

Apr. 25, 1989 [JP] Japan .................................. 1-48359

[51] Int. Cl.⁵ .......................... F27D 11/06; H05B 3/40
[52] U.S. Cl. ....................................... 219/385; 219/521
[58] Field of Search ............... 219/385, 386, 387, 439, 219/462, 399, 521; 126/113

[56] References Cited

U.S. PATENT DOCUMENTS

| 999,257 | 8/1911 | Radtke ................................ 219/521 |
| 2,807,701 | 9/1957 | Conlin et al. ....................... 219/521 |
| 2,907,861 | 10/1959 | Melton ................................ 219/521 |
| 4,950,870 | 8/1990 | Mitsuhashi et al. ................. 219/390 |

FOREIGN PATENT DOCUMENTS 62-12312 1/1987 Japan .

Primary Examiner—Teresa J. Walberg
Assistant Examiner—Tuan Vinh To
Attorney, Agent, or Firm—Fleit, Jacobson, Cohn, Price, Holman & Stern

[57] ABSTRACT

A multi-use type heating apparatus is disclosed having a heat-generating body as a heat source, receptacle-type heating chambers provided integrally therewith for internally accommodating objects to be heated, the heating chambers being arranged around the heat-generating body at a predetermined distance remote from the heat-generating body, a heat transmission medium to be filled in the heating chambers, together with any objects to be heated, and a working mechanism for setting the heat-radiating temperature of the heat-generating body.

8 Claims, 3 Drawing Sheets

MULTI-USE TYPE HEATING APPARATUS

DETAILED EXPLANATION OF THE INVENTION

1. Industrial Utility Field

This invention relates to a multipurpose heating apparatus usable for sterilization of injection syringes, surgeon's knives, forcepses, or heating for solution of impression materials for modeling such as agar, wax, etc.

2. Conventional Arts

Heating apparatus of this kind is installed in consultation rooms, operating rooms, etc. for use and materials to be heated are heated at proper temperature so as to be thermally treated for solution, and as a prior art there is disclosed Japanese Utility Model Laid-open No. Sho-62-12312.

TECHNICAL PROBLEMS

The heating apparatus, however, disclosed in the above-described invention is only a monocapacity one having a mechanism for heating materials to be heated to the temperature of necessity only and the use is very much limited.

An object of this invention is to solve the said problems and to provide a multipurpose heating apparatus capable of using heating mediums of plural kinds for heating plural kinds of materials to be heated by only one piece of apparatus.

Another object of the present invention is to provide a multipurpose heating apparatus capable of changing the heating temperature without changing the heater capacity and the electric power.

TECHNICAL MEASURES

The above-described objects are attained by a heating apparatus having a heat-generating body and plurality of heating chambers provided integrally with the heat-generating body at a location a predetermined distance remote from the heat-generating body and heat transmitting measures such as water, oil, beads or air etc. to be filled in an accommodation chamber, and a working mechanism for setting the heat radiating temperature of the afore-mentioned heat-generating body.

The heat-generating body is used as a heating source in the heating apparatus of the present invention and the type of heaters of the electric heat converter shown in the embodiment is most suitable.

A working mechanism is provided for setting the heat radiating temperature of a heat-generating body like this electric heater and such a mechanism does control the temperature of the heat-generating body itself. There are interposed heat-transmitting measures between the heat-generating body and the object to be heated and are used to change the heating temperature for the object to be heated.

BRIEF EXPLANATION OF DRAWINGS

The drawings shown an embodiment of the present invention, wherein.

EMBODIMENT

Figure 1:
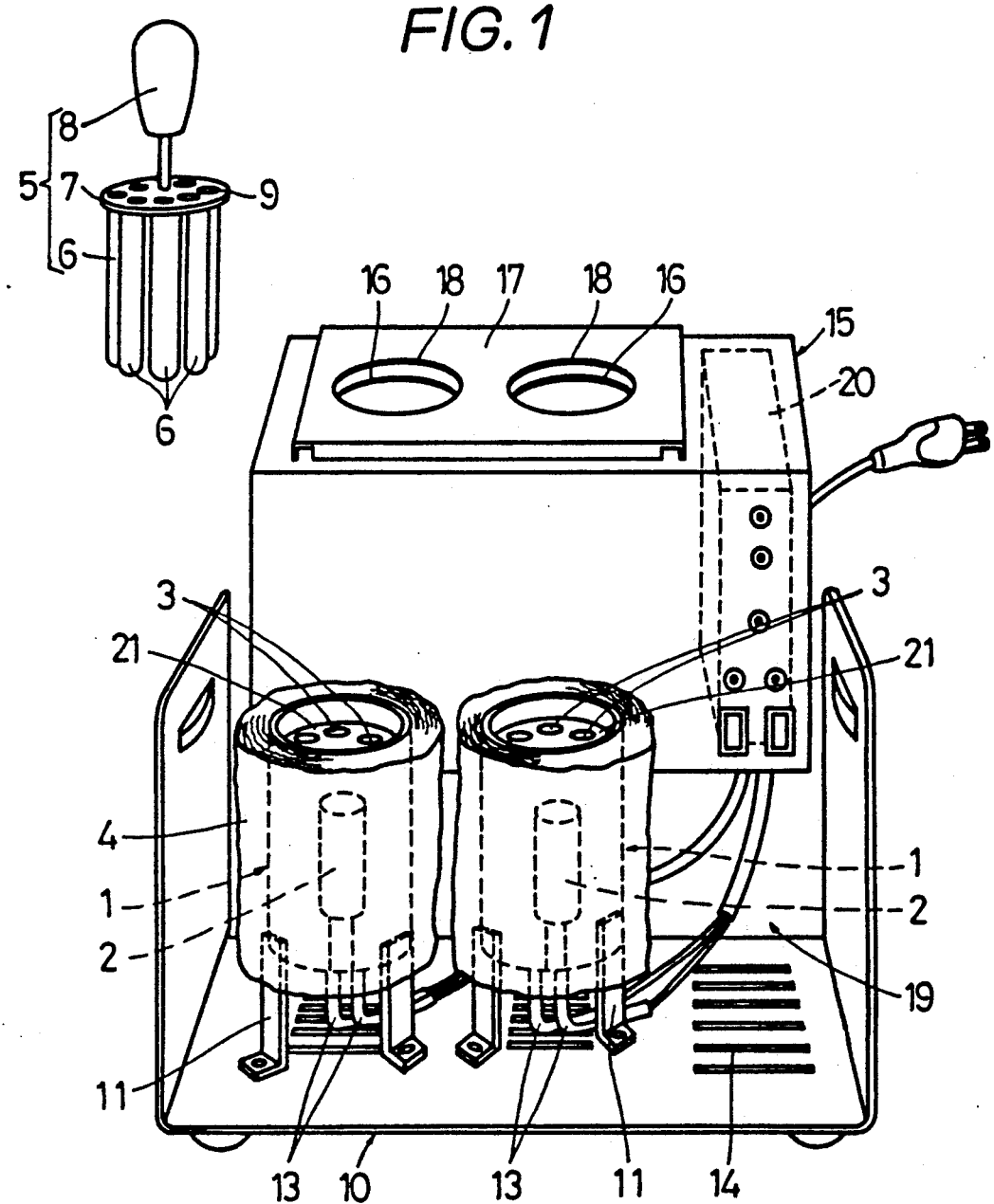
FIG. 1 is a perspective view exposing the internal part with the outer frame removed off.
Figure 2:
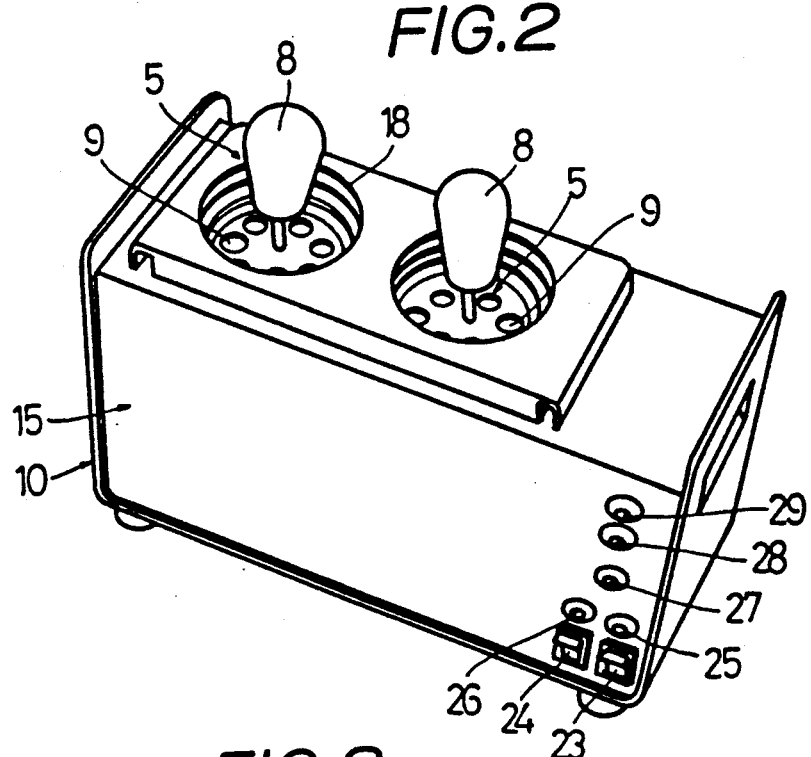
FIG. 2 is a perspective view of the total body.
Figure 3:
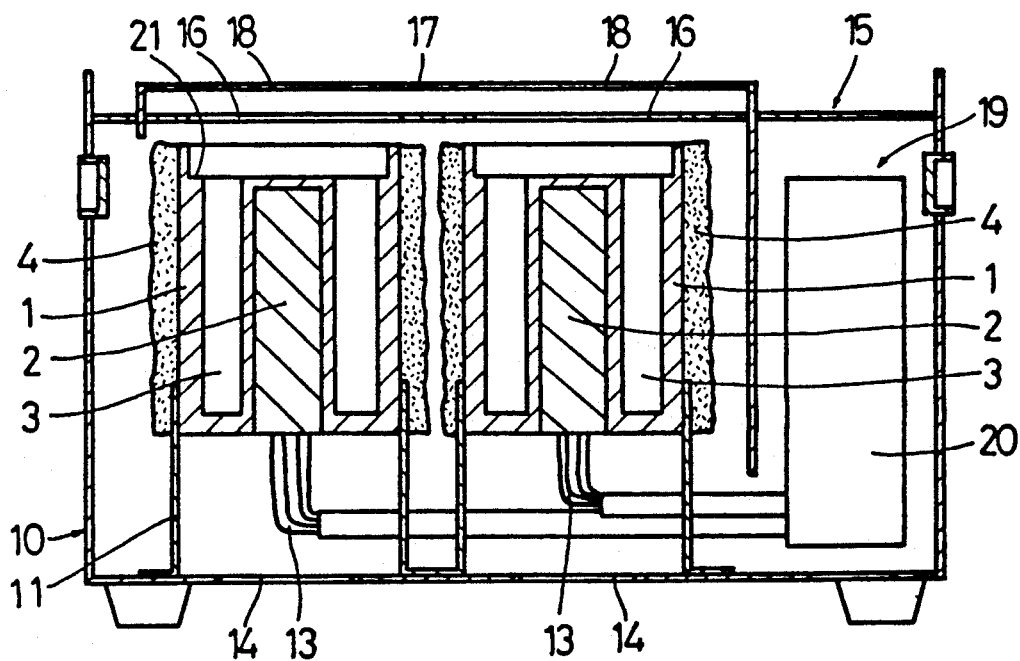
FIG. 3 shows a longitudinal sectional view thereof.

In the following, the invention will be explained with reference to the drawings.

The apparatus shown as an example is a portable one which is comparatively of small thermal capacity, wherein the heating apparatus 1 in the form of a heater body is disposed in two sets facing upwardly on the base of the base frame 10 by means of the supporting pillars 11.

The heating apparatus 1 is formed in a cylindrical form with a bottom base in the centre, of which there is formed an accommodation chamber opening downwardly and there is provided a heater of the type of electric thermal converter as a heat-generating body 2.

The heating chamber 3 is provided in plural number in parallel with and at an equal interval and equal distance therewith with the said heat-generating body as the centre.

The temperature in each heating chamber 3 becomes equal, because the heating chambers 3 of plural number are arranged concentrically around the heat-generating body 2.

The heater body itself of the heating apparatus can be formed of such a construction from metal of good thermal conductivities by shaping or metal casting.

Numeral 4 shows the adiabatic body made from asbestos wound around the outer surface of the body of the heating apparatus; 13 is heater-cord; and 14 is an air-port.

The reference numeral 15 is an outer frame fitted to the base frame 10 by means of screwing etc. and covers the heating apparatus 1, etc. so as to construct the outer packaging portion of the heating apparatus together with the base frame 10.

On the upper surface of this outer frame 15 there are two round openings 16 for access to the said two sets of heating apparatus: moreover, above the outer frame, there is a protection plate 17 arranged with a little interspace therefrom and in the protection plate there are two operating openings 18 of the same diameter with the round openings 16.

The reference numeral 19 is a space formed between the base frame 10 and the outer frame 15; 20 is a working mechanism contained adiabatically in said space 19 and electrically works to set the heat-radiating temperature of the heating apparatus 1.

The working mechanism 20 does electrically adjust the output of the heating apparatus 1 and any known electric adjusting mechanism can be used.

The heat-receiving body 5 is designed to be detachably insertable into the plural number of heating chambers 3 of longitudinal pore shape and is provided with base having accommodation pipes 6 in the same number with the heating chambers 3, a brim plate 7 for fixing each accommodation pipe 6 at its circumferential portion of the opening part, and a knob 8 provided in the centre of the brim plate 7 so as to be projected upwardly, said brim plate 7 having an opening 9 for allowing internally therethrough objects to be heated as well as thermal conductors, and also it has a diameter suitable for being insertable into a recessed portion 21 provided at the upper part of the cylindrical body of the heating apparatus 1.

Figure 4:
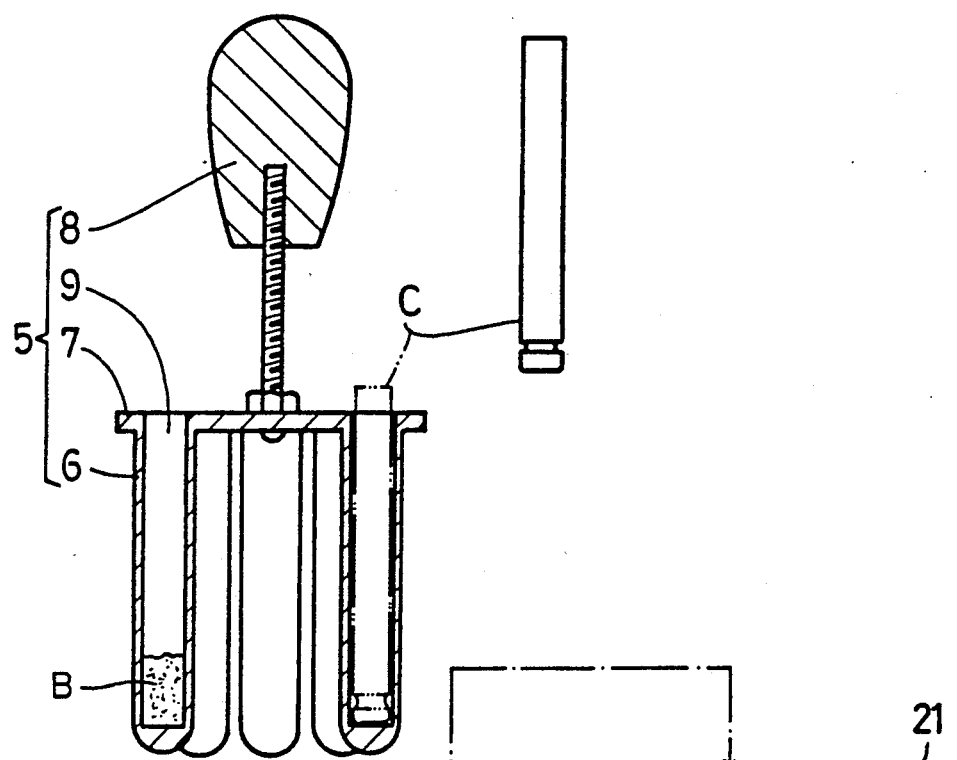
FIG. 4 is an expanded sectional view of the main portions.
Figure 5:
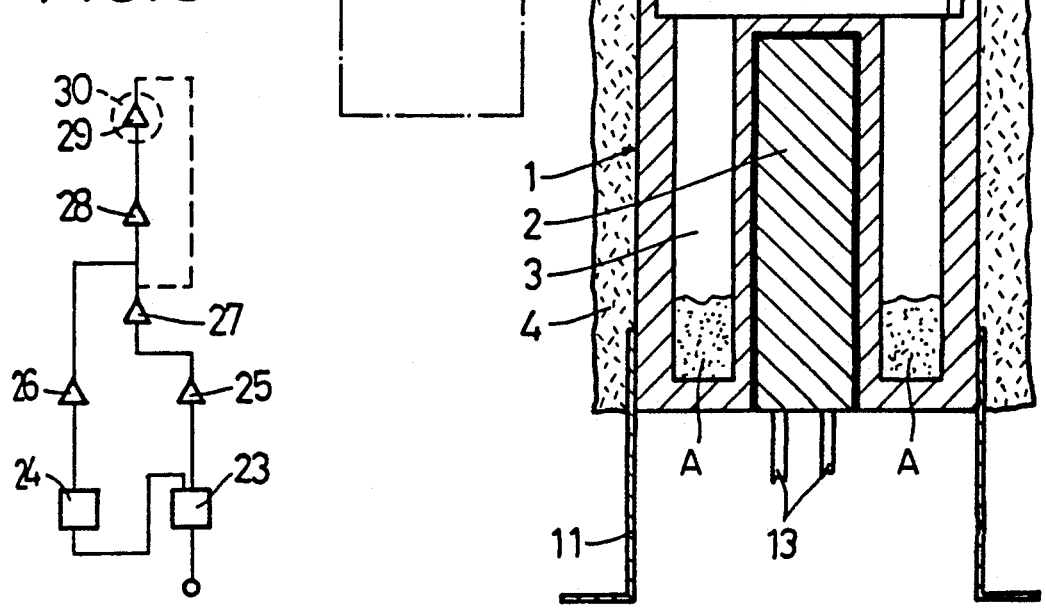
FIG. 5 is a block view of the pilot lamp relations.

The thermal conductors are filled within the heating chambers 3, as shown at A in FIG. 4 or the accommodation pipes 6 as shown at B and are used in the order of smaller thermal conductivities such as air, liquid of oil (e.g., oil of telebinth), water. etc. and also solids of ceramics, bead, etc.

The above-named elements are for changing the heating temperature for objects to be heated which are inserted into the heating chambers 3 and/or the accommodation pipes 6, and the temperature of less than 100° C. in the case of air, about 100° C. in the case of water, about 200° C. when in oil, and more than 300° C. in the case of ceramics could be obtained, respectively.

In each of the drawings, 23 is a switch of the electric source of the present apparatus; 24 is a switch which is able to work the heating apparatus 1; 25 is an electric source pilot lamp; 26 is a heating apparatus working pilot lamp; 27 is a heating apparatus lagging pilot lamp; 28 is a heating apparatus melting pilot lamp; 29 is a melting operation completion pilot lamp; and 30 is a melting operation completion advising bother.

OPERATION

In the construction described above, when the heating chambers 3 or heat-receiving bodies 5 are used, the accommodation pipes 6 are filled with thermal conductors suitable for the objects to be heated (in the case of air, the accommodation pipes are allowed with their openings kept opened) and by switching on the switches 23, 24, it is possible to heat the objects to be heated with the required temperature. The following is an example:

| Thermal conductor | Heating temperature | Object to be heated |
|---|---|---|
| Air | 95° C. | Gelatin for impression |
| Water | 100° C. | Injection syringes; Scalpels; Extractors; Gelatin |
| Oil | 200° C. | Injection syringes; Scalpels; Extractors |
| Ceramics Beads | 320° C. | Round bars, etc. (Pre-heating); Dentist's reamers; Fasteners |

In the table, gelatin is a material of shaping to be used in forming shapes of gum or teethbridges at dentists' and is heated for melting; injection syringes, scalpels, etc. are for the purpose of sterilization by heat, and round bars, etc. are for soldering and are for pre-heating before the working.

Especially, the apparatus shown as an example is suitable also for heating the gelatin contained in a cartridge C, in which case it may be possible to use the heating chambers 3 of the heating apparatus 1 or the accommodation pipes 6 of the heat-receiving body 5 to be inserted thereinto of one side as a furnace, and the heating chambers 3 or the accommodation pipes 6 of the other side may be used for lagging of the gelatin after finishing the melting.

In this case, for the heating chambers 3 or the accommodation pipes 6 of one side it may be possible to use oil or ceramics, beads, etc. and for the heating chambers 3 or the accommodation pipes 6 of the other side air may be used as the thermal conductors and no other temperature adjustment is required in particular. Of cource, it may be free to add any construction for changing the heater capacity.

EFFECTS

Since this invention is constructed as described above, it may be possible to change the temperature for heating objects to be heated in accordance with the thermal conductivities of the thermal conductors filled within a plurality of heating chambers (when heat-receiving bodies are used, their accommodation pipes) so that this apparatus is provided with multi-usabilities to be used for heating plural kinds of objects to be heated by one single piece and as the setting of the heating temperature can be performed without the necessity for example of operation for increasing or decreasing the electric power, the operation is easy and at the same time reduction of electric power is possible in some cases so that the effects of the invention is clear and apparent.

I claim:

1. A heating apparatus of multi-use type comprising a thermally conductive heater body formed with a central elongate bore and further elongate bores surrounding the central bore, the further bores defining heating chambers, a heat-generating body disposed in the central bore, the heating chambers disposed at locations remote from said heat-generating body, flowable thermal conduction medium in at least one of said heating chambers, and a working mechanism for setting a heat-radiating temperature of said heat-generating body.

2. A heating apparatus of multi-use type as claimed in claim 1, wherein said heat-generating body comprises a heater of electric heat conversion types, said heat-generating body being disposed centrally of said heating chambers which are arranged at an equal space and an equal distance from said body.

3. A heating apparatus of multi-use type as claimed in claim 2, wherein said heating apparatus is provided with an adiabatic body, wound over an outer surface of said heater body.

4. A heating apparatus as claimed in claim 3 wherein said heater body is supported on posts above a base.

5. A heating apparatus of multi-use type as claimed in claim 1, wherein the apparatus is replicated in a common housing.

6. A heating apparatus of multi-use type as claimed in claim 1, further including a heat-receiving body having a plurality of accommodation pipes to be inserted into the respective heating chambers.

7. A heating apparatus of multi-use type as claimed in claim 5, wherein said heat-receiving body is provided with a brim plate fitted integrally with said accommodation pipes and a knob fitted to said brim plate.

8. A heating apparatus as claimed in claim 6 further including flowable thermal conduction medium in at least one of said pipes.

* * * * *